United States Patent [19]

Spargo

[11] Patent Number: 6,046,338
[45] Date of Patent: Apr. 4, 2000

[54] SEPARATION OF THE ENANTIOMERS OF AMLODIPINE VIA THEIR DIASTEREOMERIC TARTRATES

[75] Inventor: Peter Lionel Spargo, Sandwich, United Kingdom

[73] Assignee: Pfizer Inc., New York, N.Y.

[21] Appl. No.: 09/071,810

[22] Filed: May 5, 1998

Related U.S. Application Data

[62] Division of application No. 08/704,612, filed as application No. PCT/EP95/00847, Mar. 6, 1995, Pat. No. 5,750,707.

[30] Foreign Application Priority Data

Mar. 24, 1994 [GB] United Kingdom .................... 9405833

[51] Int. Cl.$^7$ ..................... C07D 213/80; C07D 213/803
[52] U.S. Cl. ............................................. 546/322; 546/321
[58] Field of Search ...................... 546/321, 322

[56] References Cited

U.S. PATENT DOCUMENTS

| | | | |
|---|---|---|---|
| 5,037,987 | 8/1991 | Herrmann et al. | 546/123 |
| 5,064,839 | 11/1991 | Flockerzi | 514/318 |
| 5,162,345 | 11/1992 | Sameraro et al. | 514/356 |
| 5,326,772 | 7/1994 | Klemm et al. | 514/318 |
| 5,364,872 | 11/1994 | Tamazawa et al. | 514/343 |

FOREIGN PATENT DOCUMENTS

| | | |
|---|---|---|
| 0160451 | 4/1985 | European Pat. Off. . |
| 0240828 | 3/1987 | European Pat. Off. . |
| 0242829 | 4/1987 | European Pat. Off. . |
| 0314038 | 11/1988 | European Pat. Off. . |
| 0331315 | 2/1989 | European Pat. Off. . |
| 0365140 | 9/1989 | European Pat. Off. . |
| 0383320 | 2/1990 | European Pat. Off. . |
| 0385423 | 2/1990 | European Pat. Off. . |
| 3628215 | 8/1986 | Germany . |

OTHER PUBLICATIONS

Hungerbhler et. al., Angewandte Chemie Int. Edu. Engl., 18(12), 958–960, (1979).
Goldmann, S. and Stoltefuss, J., Angew Chem. Int. Ed. Engl., vol. 30, pp. 1559–1578 (1991).

Merck Index, 11th Edition, New York, 1982, pp. 1432–1433, Entries 9037–9040.

Jacques, J. et al., Enantiomers, Racemates and Resolutions, pp. 259, 385 Krieger Publisher, Co. (1981).

Oi et al., Journal of Liquid Chromatography, 16(4), 893–901 (1993).

Organikum, 16th Auglage VEB, Berlin, 1986, p. 525.

J. E. Arrowsmith et al., J. Med Chem., 1986, 29, 1696.

S. Goldman et al., J. Med. Chem., 1992, 35, 3341.

*Primary Examiner*—Alan L. Rotman
*Attorney, Agent, or Firm*—Peter C. Richardson; Gregg C. Benson; James T. Jones

[57] ABSTRACT

A method for the separation of R-(+)- and S-(−)-isomers of amlodipine (I) from mixtures thereof, which comprises the reaction of the mixture of isomers with either L- or D-tartaric acid in an organic solvent containing sufficient dimethyl sulphoxide (DMSO) for the precipitation of, respectively, a DMSO, solvate of an L-tartate salt of R-(+)-amlodipine, or a DMSO solvate of a D-tartrate salt of S-(−)-amlodipine.

(I)

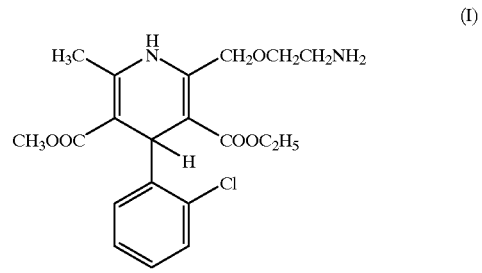

9 Claims, No Drawings

SEPARATION OF THE ENANTIOMERS OF AMLODIPINE VIA THEIR DIASTEREOMERIC TARTRATES

This is a divisional of application Ser. No. 08/704,612 filed Sep. 18, 1996 U.S. Pat. No. 5,750,707, which is a National Stage filing under 35 USC §371 based on PCT/EP95 00847 which was filed internationally on Mar. 6, 1995.

The invention described herein provides an efficient method for the separation of the optical isomers of amlodipine via salt formation with tartaric acid in the presence of dimethyl sulphoxide.

BACKGROUND

Amlodipine 1a, and its salts are long-acting calcium channel blockers, and are thus useful for the treatment of cardiovascular disorders, such as angina, hypertension and congestive heart failure. The two enantiomers of amlodipine, and their salts, have different pharmacological profiles. The S-(−)-isomer is the more potent calcium channel blocker, and the R-(+)-isomer also exhibits activity in the treatment or prevention of atherosclerosis.

J. E. Arrowsmith et al in *J.Med.Chem* (1986) 29 1696, described the preparation of the two enantiomers of amlodipine via separation of the diastereotopic azide esters 1b, and J. E. Arrowsmith, in EPA 331315, disclosed the use of cinchonidine salts of acid 1c for the resolution of intermediates to eventually give enantiomerically pure amlodipine isomers. S. Goldman et al, in *J.Med.Chem.* (1992) 35 3341, described the chromatographic separation of diastereomeric amide isomers 1d.

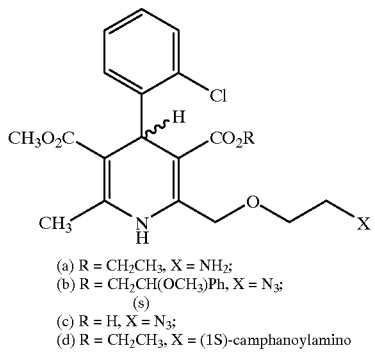

1

(a) R = CH$_2$CH$_3$, X = NH$_2$;
(b) R = CH$_2$CH(OCH$_3$)Ph, X = N$_3$;
    (s)
(c) R = H, X = N$_3$;
(d) R = CH$_2$CH$_3$, X = (1S)-camphanoylamino None of the disclosed methods for resolution of amlodipine intermediates or derivatives offer an efficient and economic method susceptible of industrial application. Other methods of providing enantiomerically enriched amlodipine isomers are thus needed.

A recent review by S. Goldman et al, in *Angew.Chem.Int.Edn.(Engl.)* (1991) 30 1559, describes various methods of providing chiral 1,4-dihydropyridines in high enantiomeric excess (e.e.). This review paper, in section 2.2 (Resolution of Racemic Mixtures of Basic Dihydropyridine Derivatives), states that "Chiral acids such as camphorsulphonic acid and substituted tartaric acids have been used to separate the enantiomers of basic dihydropyridine derivatives in yields of up to 30%" (emphasis added). The use of these methods for the resolution of amlodipine into its enantiomers gave unsatisfactory results, in terms of both yield and enantiomeric purity. The "substituted tartaric acid" used most commonly in the reported methods was O,O'-dibenzoyltartaric acid, and various solvents, most commonly alcohols, were used with this reagent.

THE INVENTION

We herein describe a new, simple, economic and efficient process for preparing both enantiomers of amlodipine 1a and their salts, in unexpectedly good yield andenantiomeric purity. The invention provides a method for the separation of the R-(+)-and S-(−)-isomers of amlodipine from mixtures thereof, which comprises the reaction of the mixture of isomers with either L- or D-tartaric acid in an organic solvent containing sufficient dimethyl sulphoxide (DMSO) for the precipitation of, respectively, a DMSO solvate of an L-tartrate salt of R-(+)-amlodipine, or a DMSO solvate of a D-tartrate salt of S-(−)-amlodipine. The use of both tartaric acid and DMSO are essential to this unique separation process.

Preferably, either about 0.5 mole or about 0.25 mole of either L- or D-tartaric acid per mole of amlodipine is used.

Preferably, the precipitate is a hemitartrate monosolvate of amlodipine. These solvates also form part of the invention.

Following separation of the precipitate, which may be carried out by methods well-known in the art, for example by filtration, centrifugation or decantation, either the precipitate or the filtrate or supernatant, now suitably enriched in the desired isomer, can be processed further. As is well-known in the art, the further processing method applicable to one diastereomer may be equally applied to its antipode.

The precipitated DMSO-solvate may be treated further in a number of ways. Recrystallisation from an organic solvent can give the amlodipine tartrate free from DMSO. This can further be treated with a base to give the free enantiomerically-pure amlodipine isomer. The precipitated DMSO-solvate may also be treated with a base to give the optically-pure amlodipine free base directly, without the need for isolation of the amlodipine tartrate.

The filtrate or supernatant remaining, after removal of the amlodipine tartrate DMSO solvate precipitate, may also be processed further. Removal of part of the remaining solvent may give a further crop of the original amlodipine tartrate DMSO solvate precipitate which may be removed in the same manner as mentioned before. Alternatively, the filtrate or supernatant may be treated with the antipode of the tartaric acid used originally, which results in precipitation of the antipodal amlodipine isomer tartrate solvate. This proceeds particularly well when about 0.25 mole of tartaric acid is used per mole of amlodipine (see Example 9). Addition of a different solvent to the filtrate or supernatant may also encourage precipitation. Alternatively, the original remaining filtrate or supernatant may be treated with a base, either with or without prior removal of solvent, which may be then worked-up by methods well-known in the art, to give the amlodipine isomer or its salts where the amlodipine is the enantiomer of that which precipitated originally. It is understood that various combinations and repetitions of the above steps may be carried out to optimise the obtention of desired yields and optical purities. Thus it is possible to isolate both enantiomers efficiently from a mixture thereof.

The preferred solvents for carrying out the resolution are DMSO, and DMSO with a co-solvent or co-solvents selected from well-known solvents such as ketones, alcohols, ethers, amides, esters, chlorohydrocarbons, water, nitriles and hydrocarbons. Preferred ketones are acetone and methyl ethyl ketone (MEK). Preferred alcohols are C$_1$–C$_7$ saturated alcohols such as propan-2-ol. Preferred ethers are diethyl ether and tetrahydrofuran (THF). Preferred amides are N,N-dimethylformamide (DMF), N,N- dimethylacetamide (DMAC) and N,N'-dimethylpropyleneurea (DMPU). Preferred esters are acetates such as ethyl acetate. Preferred chlorohydrocarbons are chloroform, dichloromethane, 1,2-dichloroethane and 1,1,1-trichloroethane. Preferred nitriles are $C_2$–$C_7$ nitriles such as acetonitrile. Preferred hydrocarbons are $C_5$–$C_{10}$ hydrocarbons such as toluene.

The maximum amount of co-solvent which can be present in the DMSO varies accordingly to the specific co-solvent employed and a man skilled in the art will readily be able to establish the appropriate quantity which in each particular case will give the required precipitate of the DMSO solvate. Preferably, the co-solvent is present in an amount of from 0.2 to 6% by volume based on the volume of the DMSO.

In some cases, e.g. with acetone, the co-solvent may be present in an amount of up to 50% v/v of the total solvent mixture.

Preferred methods of separation of the DMSO solvate precipitate are filtration and centrifugation. Especially preferred is filtration.

Preferred recrystallisation solvents for the tartrate salt are alcohols, such as methanol.

Preferred bases for the preparation of amlodipine from its salts are metal hydroxides, oxides, carbonates, bicarbonates and amides. Especially preferred are alkali metal hydroxides and oxides, such as sodium hydroxide.

The process is characterised by reacting racemic or partially-resolved amlodipine 1a with optically active tartaric acid in DMSO with or without a co-solvent. This results in a crystalline precipitate being formed, which can be separated by filtration. Analysis of the crystalline precipitate obtained in the following specific Examples showed the incorporation of approximately 1 mole equivalent of DMSO and 0.5 mole equivalent of tartaric acid per mole of amlodipine. An illustration of the process using D-tartaric acid is provided in the scheme below:

proviso that DMSO is present in sufficient amount to allow precipitation of the DMSO solvate to take place.

The invention is illustrated by the following Examples.

Optical purities were measured by chiral HPLC. The HPLC conditions used for this separation were as follows: Column—Ultron ES-OVM, Ovomucoid—15 cm; Flow rate—1 ml/min; Detection wavelength—360 nm; Eluent—Disodium hydrogenphosphate buffer (20 mM,ph7): acetonitrile, 80:20. Samples were dissolved in acetonitrile:water, 50:50, 0.1 mg/ml solution.

EXAMPLE 1

(S)-(−)-Amlodipine-hemi-D-tartrate-mono-DMSO-solvate from (R,S)-amlodipine

To a stirred solution of 114.27 g (R,S)-amlodipine in 558 ml DMSO was added a solution of 21 g D-(−)-tartaric acid (0.5 mole equivalents) in 558 ml DMSO. Precipitation began within 5 minutes, and the resulting slurry was stirred at room temperature overnight. The solid was collected by filtration, washing with 500 ml DMSO followed by 500 ml acetone. It was then dried at 50° C. in vacuo overnight to give 71.3 g (91% of theoretical yield) (S)-(−)-amlodipine-hemi-D-tartrate-mono-DMSO-solvate, m.p. 158–160° C., (Found: C 51.28%, H 6.10%, N 4.93%; Calc. for $C_{20}H_{25}N_2O_5Cl.0.5[C_4H_6O_6].C_2H_6OS$: C 51.29%, H 6.10%, N 4.98%), 98% d.e. by chiral hplc.

EXAMPLE 2

(S)-(−)-Amlodipine-hemi-D-tartrate-monohydrate from (S)-(−)-amlodipine-hemi-D-tartrate-mono-DMSO-solvate 50 g (S)-(−)-Amlodipine-hemi-D-tartrate-mono-DMSO-solvate was dissolved in 250 ml refluxing methanol. On cooling, a solid precipitated, and the slurry was stirred

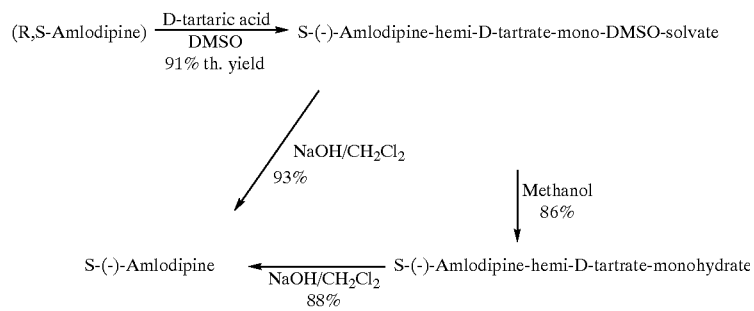

It is understood that L-tartaric acid can also be used, in which case it is the R-(+)-amlodipine isomer which forms the precipitate. It is also to be understood that once the precipitate has been formed, it can be further treated in a number of ways, for example to provide the free base, as illustrated above, or to provide alternative salts and/or solvates of amlodipine isomers. It is also to be understood that by virtue of the fact that a separation (or partial separation) of a particular enantiomer takes place, the resulting filtrate is thereby enriched with the opposite enantiomer (antipode), which may also be processed further, in a similar manner. This proceeds particularly well when about 0.25 mole of tartaric acid is used per mole of amlodipine. Co-solvents can be used in the resolution step, and can contribute to economy, ease of handling, etc., with the overnight at room temperature. The solid was collected by filtration, washing with 150 ml methanol, then dried at 50° C. in vacuo overnight to give 38.4 g (86%) (S)-(−)-amlodipine-hemi-D-tartrate-monohydrate, m.p. 134–137° C., (Found: C 52.67%, H 6.25%, N 5.49%; Calc. for $C_{20}H_{25}N_2O_5Cl.0.5[C_4H_6O_6].H_2O$: C 52.64%, H 6.02%, N 5.58%/), 98% d.e. by chiral hplc.

EXAMPLE 3

(S)-(−)-Amlodilpine from (S)-(−)-amlodipine-hemi-D-tartrate-monohydrate 30 g (S)-(−)-Amlodipine-hemi-D-tartrate-monohydrate was slurried in 230 ml $CH_2Cl_2$ and 230 ml 2N NaOH(aq) for 20 minutes. The organic solution was then separated off and washed once with water. The $CH_2Cl_2$ was distilled off and replaced with hexane, giving a slurry. The solid was collected by filtration and dried at 50° C. in vacuo overnight to give 21.6 g (88%) (S)-(−)-amlodipine, m.p. 108–110° C., (Found: C 58.57%, H 6.37%, N 6.76%: Calc. for $C_{20}H_{25}N_2O_5Cl$: C 58.75%, H 6.16%, N 6.85%), $[\alpha]_D^{25}$−32.5° (c=1,MeOH), 98.4% e.e. by chiral hplc.

EXAMPLE 4

(S)-(−)-Amlodipine from (S)-(−)-amlodipine-hemi-D-tartrate-mono-DMSO-solvate 5 g (S)-(−)-Amlodipine-hemi-D-tartrate-mono-DMSO-solvate was slurried in 56 ml $CH_2Cl_2$ and 56 ml 2N NaOH(aq) for 40 minutes. The organic solution was then separated and washed once with water. The $CH_2Cl_2$ was distilled off and replaced with hexane, giving a slurry. The solid was collected by filtration and dried at 50° C. in vayuo overnight to give 3.39 g (93%) (S)-(−)-amlodipine, m.p. 107–110° C., (Found: C 58.31%, H 6.57%, N 6.50%: Calc. for $C_{20}H_{25}N_2O_5Cl$: C 58.75%, H 6.16%, N 6.85%), $[\alpha]_D^{25}$−28.5° (c=1,MeOH), 97% e.e. by chiral hplc.

EXAMPLE 5

(R)-(+)-Amlodipine-hemi-L-tartrate-mono-DMSO-solvate from (R,S)-amlodipine

To a stirred solution of 114.27 g(R,S)amlodipine in 558 ml DMSO was added a solution of 21.0 g (0.5 mole equivalents) L-(−)-tartaric acid in 558 ml DMSO. Precipitation began within 5 minutes, and the resulting slurry was stirred at room temperature overnight. The solid was collected by filtration, washing with 500 ml DMSO followed by 500 ml acetone. It was then dried at 50° in vacuo overnight to give 67.0 g (85% of theoretical yield) (R)-(+)-amlodipine-hemi-L-tartrate-mono-DMSO-solvate, m.p. 159–161° C., (Found: C 51.27%, H 6.08%, N 4.91%; Calc. for $C_{20}H_{25}N_2O_5Cl.0.5[C_4H_6O_6].C_2H_6OS$: C 51.29%, H 6.10%, N 4.98%), 98% d.e. by chiral hpic.

EXAMPLE 6

(R)-(+)-Amlodipine-hemi-L-tartrate-monohydrate from (R)-(+)-amlodipine hemi-L-tartrate-mono-DMSO-solvate 40g (R)-(+)-Amlodipine-hemi-L-tartrate-mono-DMSO-solvate was dissolved in 200 ml refluxing methanol. On cooling, a solid precipitated, and the slurry was stirred overnight at room temperature. The solid was collected by filtration, washing with 120 ml methanol, then dried at 50° C. in vacuo overnight to give 30.0 g (84%) (R)-(+)-amlodipine-hemi-L-tartrate-monohydrate, m.p. 132–135° C., (Found: C 52.68%, H 6.23%, N 5.46%; Calc. for $C_{20}H_{25}N_2O_5Cl.0.5[C_4H_6O_6].H_2O$: C 52.64%, H 6.02%, N 5.58%), 97.5% d.e. by chiral hpic.

EXAMPLE 7

(R)-(+)-Amlodipine from (R)-(+)-amlodipine-hemi-L-tartrate-monohydrate 25 g (R)-(+)-Amlodipine-hemi-L-tartrate-monohydrate was slurried in 200 ml $CH_2Cl_2$ and 200 ml 2N NaOH(aq) for 20 minutes. The organic solution was then separated off and washed once with water. The $CH_2Cl_2$ was distilled off and replaced with hexane, giving a slurry. The solid was collected by filtration and dried at 50° C. in vacuo overnight to give 17.8 g (87%) (R)-(+)-amlodipine, m.p. 108–110° C., (Found: C 58.67%, H 6.24%, N 6.76%: Calc. for $C_{20}H_{25}N_2O_5Cl$: C 58.75%, H 6.16%, N 6.85%), $[\alpha]_D^{25}$+28.3° (c=1, MeOH), 97.5% e.e. by chiral hplc.

EXAMPLE 8

(R)-(+)-Amlodipine from (R)-(+)-amlodipine-hemi-L-tartrate-mono-DMSO-solvate 5 g (R)-(+)-Amlodipine-hemi-L-tartrate-mono-DMSO-solvate was slurried in 56 ml $CH_2Cl_2$ and 56 ml 2N NaOH(aq) for 40 minutes.

The organic solution was then separated and washed once with water. The $CH_2Cl_2$ was distilled off and replaced with hexane, giving a slurry. The solid was collected by filtration and dried at 50° C. in vacuo overnight to give 3.43 g (94%) (S)(−)-amlodipine, m.p. 106–109° C., (Found: C 58.26%, H 6.69%, N 6.43%: Calc. for $C_{20}H_{25}N_2O_5Cl$: C 58.75%, H 6.16%, N 6.85%), $[\alpha]_D^{25}$+29.90° (c=1, MeOH), 98.5% e.e. by chiral hplc.

EXAMPLE 9

(S)-(−)Amlodipine-hemi-D-tartrate-mono-DMSO-solvate and (R)-(+)-amlodipine-hemi-L-tartrate-mono-DMSO-solvate from (R,S)-amlodipine To a stirred solution of 1.02 g of (R,S)-amlodipine in 5 ml of DMSO was added a slurry of 0.099 g (0.25 mole equivalents) of D-tartaric acid in 5 ml of DMSO. The resulting mixture was then left to stir overnight and the solid which formed was filtered off, washed with 2 ml of acetone and dried at 50° C. in vacuo overnight to give 0.47 g (67% of theoretical yield) (S)-(−)-amlodipine hemi-D-tartrate-mono-DMSO-solvate; m.p. 159–162° C., (Found: C 51.45%, H 6.13%, N 4.77%; Calc. for $C_{20}H_{25}N_2O_5Cl.0.5[C_4H_6O_6].C_2H_6OS$: C 51.29%, H 6.10%, N 4.98%), >99.5% d.e. by chiral hplc. To the filtrate was then added 0.099 g (0.25 mole equivalents) of L-tartaric acid, the mixture was then left to stir overnight and the solid formed filtered off and washed with 2 ml of acetone and dried at 50° C. in vacuo to give 0.33 g (47% of theoretical yield) (R)-(+)-amlodipine-hemi-L-tartrate-mono-DMSO-solvate; m.p. 159–162° C., (Found: C 51.49%, H 6.12%, N 4.85%; Calc. for $C_{20}H_{25}N_2O_5Cl.$ $0.5[C_4H_6O_6].C_2H_6OS$: C 51.29%, H 6.10%, N 4.98%), >99.5% d.e. by chiral hplc.

EXAMPLE 10

(S)-(−)Amlodipine-hemi-D-tartrate-mono-DMSO-solvate and (R)-(+)-amlodipine-hemi-L-tartrate-mono-DMSO-solvate from (R,S)-amlodipine The method of Example 9 was used, but substituting the DMSO with a 50:50 v/v DMSO/acetone mixture.

Yield of (S)-(−)-amlodipine-hemi-D-tartrate-mono-DMSO-solvate=0.22 g (31% of theoretical yield) m.p. 160–163° C., (Found C 51.13%, H 6.03%, N 4.91%; Calc. for $C_{20}H_{25}N_2O_5Cl.0.5[C_4H_6O_6].C_2H_6OS$:C 51.29%, H 6.10%, N 4.90%). 99.5% d.e. by chiral hplc.

Yield of (R)-(+)-amlodipine-hemi-L-tartrate-mono-DMSO-solvate=0.19 g (27% of theoretical yield), m.p. 160–163° C., (Found: C 51.39%, H 6.01%, N 4.82%; Calc. for $C_{20}H_{25}N_2O_5Cl.0.5[C_4H_6O_6].C_2H_6OS$: C 51.29%, H 6.10%, N 4.98%), 98% d.e. by chiral hplc.

EXAMPLE 11

(S)-(−)-Amlodipine-hemi-D-tartrate-mono-DMSO-solvate

The method of Example 1 was repeated using the same molar ratios but using DMSO to which a co-solvent has been added as set out in the Table. The percentages are in v/v. The solvate can then be processed to S-(−)-amlodipine according to the procedures of Examples 2–4.

TABLE

| Co-solvent | % By volume of the co-solvent | Diastereomeric excess by hplc |
|---|---|---|
| H$_2$O | 0.25% | 96.8% de. |
| H$_2$O | 0.5% | 87.7% de. |
| Acetone | 1% | 94% de. |
| Dimethylacetamide | 1% | 89% de. |
| Methyl ethyl ketone | 2% | 97% de. |
| Tetrahydrofuran | 2% | 96.7% de. |
| EtOAc | 2% | 90.4% de. |
| CH$_2$Cl$_2$ | 2% | 93.2% de. |
| Dimethylformamide | 2% | 93.2% de. |
| Toluene | 2% | 72.3% de. |
| Acetone | 5% | 95% de. |
| Isopropyl Alcohol | 5% | 95% de. |
| DMPU (see text) | 5% | 96.6% de. |
| Dimethylformamide | 5% | 93.2% de. |
| EtOAc | 5% | 79.2% de. |
| CH$_2$Cl$_2$ | 5% | 74% de. |
| Acetone | 50% | 94% de. |

I claim:

1. A method for the separation of the R-(+)- and S-(−)-isomers of amlodipine from mixtures thereof, which comprises the reaction of the mixture of isomers with either L- or D-tartaric acid in an organic solvent containing sufficient dimethyl sulphoxide (DMSO) for the precipitation of, respectively, a DMSO solvate of an L-tartrate salt of R-(+)-amlodipine, or a DMSO solvate of a D-tartrate salt of S-(−)-amlodipine.

2. A process according to claim 1 in which the solvent is DMSO.

3. A process according to claim 1 in which the solvent is a mixture of DMSO and a co-solvent, the co-solvent being present in an amount sufficient to allow precipitation of the DMSO solvate to take place.

4. A process according to claim 3, wherein the co-solvent is water or a ketone, alcohol, ether, amide, ester, chlorohydrocarbon, nitrile or hydrocarbon.

5. A process according to claim 4, wherein the co-solvent is water, acetone, dimethylacetamide, methyl ethyl ketone, tetrahydrofuran, ethyl acetate, dichloromethane, dimethylformamide, toluene, isopropyl alcohol or N,N'-dimethylpropyleneurea.

6. A process according to any one of claim 3, wherein the co-solvent is present in an amount of up to 50% v/v based on the volume of the DMSO.

7. A process according to claim 6, wherein the co-solvent is present in an amount of from 0.2 to 6% v/v.

8. A process according to claim 1, wherein the amount of L- or D-tartaric acid employed is either about 0.5 mole or about 0.25 mole per mole of amlodipine.

9. A process according to claim 1, wherein the solvate precipitated is, respectively, (S)-(−)-amlodipine-hemi-D-tartrate-mono-DMSO-solvate or (R)-(+)-amlodipine-hemi-L-tartrate-mono-DMSO-solvate.

* * * * *